(12) United States Patent
Akimova et al.

(10) Patent No.: US 11,060,126 B2
(45) Date of Patent: Jul. 13, 2021

(54) METHODS FOR DETECTING GENETICALLY MODIFIED ORGANISMS (GMO)

(71) Applicant: NUTRASOURCE PHARMACEUTICAL AND NUTRACEUTICAL SERVICES INC., Guelph (CA)

(72) Inventors: Olga Akimova, Richmond Hill (CA); Anna Deboer, Guelph (CA); Lianghong Li, Mississauga (CA); Steven Overgaard, Toronto (CA); Mike Wlodek, Cambridge (CA)

(73) Assignee: NUTRASOURCE PHARMACEUTICAL AND NUTRACEUTICAL SERVICES INC., Guelph (CA)

(*) Notice: Subject to any disclaimer, the term of this patent is extended or adjusted under 35 U.S.C. 154(b) by 115 days.

(21) Appl. No.: 15/998,965

(22) PCT Filed: Feb. 17, 2017

(86) PCT No.: PCT/CA2017/050210
§ 371 (c)(1),
(2) Date: Aug. 17, 2018

(87) PCT Pub. No.: WO2017/139898
PCT Pub. Date: Aug. 24, 2017

(65) Prior Publication Data
US 2019/0276870 A1  Sep. 12, 2019

Related U.S. Application Data

(60) Provisional application No. 62/297,386, filed on Feb. 19, 2016.

(51) Int. Cl.
| | |
|---|---|
| *C12Q 1/6806* | (2018.01) |
| *C12Q 1/686* | (2018.01) |
| *C12Q 1/06* | (2006.01) |
| *C12Q 1/6876* | (2018.01) |
| *C40B 30/04* | (2006.01) |
| *G01N 33/543* | (2006.01) |
| *G01N 33/68* | (2006.01) |
| *C12Q 1/6881* | (2018.01) |

(52) U.S. Cl.
CPC .............. *C12Q 1/06* (2013.01); *C12Q 1/6806* (2013.01); *C12Q 1/686* (2013.01); *C12Q 1/6876* (2013.01); *C12Q 1/6881* (2013.01); *C40B 30/04* (2013.01); *G01N 33/543* (2013.01); *G01N 33/68* (2013.01)

(58) Field of Classification Search
CPC ...... C12Q 1/686; C12Q 1/6806; G01N 33/68; C40B 30/04
See application file for complete search history.

(56) References Cited

U.S. PATENT DOCUMENTS

| | | |
|---|---|---|
| 9,017,947 B2 | 4/2015 | Malven et al. |
| 2003/0148278 A1 | 8/2003 | Lauter et al. |
| 2004/0161740 A1 | 8/2004 | Petiard et al. |
| 2005/0239086 A1 | 10/2005 | Lipkin et al. |
| 2006/0281096 A1 | 12/2006 | Chou et al. |

FOREIGN PATENT DOCUMENTS

| | | |
|---|---|---|
| CN | 1370841 A | 9/2002 |
| CN | 1370842 A | 9/2002 |
| CN | 101042403 A | 9/2007 |
| CN | 102827939 A | 12/2012 |
| CN | 104628860 A | 5/2015 |
| KR | 10514432 B1 | 9/2004 |
| KR | 1020040079053 A | 9/2004 |
| KR | 100707830 B1 | 4/2007 |
| KR | 1007236069 B1 | 5/2007 |
| KR | 1020080018425 A | 2/2008 |
| KR | 100838105 B1 | 6/2008 |
| KR | 1020110138691 A | 12/2011 |
| KR | 101178140 B1 | 8/2012 |
| KR | 101288403 B1 | 7/2013 |
| WO | 0132919 A3 | 5/2001 |
| WO | 2008092866 A1 | 8/2008 |

OTHER PUBLICATIONS

Lin, H-Y. et al., Detection of Genetically Modified Soybeans by PCR method and Immunoassay Kits, J. Food Drug Anal., vol. 9, pp. 160-166 (Year: 2001).*
Ermolli, M. et al., Development of an innovative immunoassay for CP4EPSPS and Cry1 AB genetically modified protein detection and quantification, Food Add. Contam., vol. 23, pp. 876-882 (Year: 2006).*
Jasbeer, K. et al., Application of DNA and Immunoassay Analytical Methods for GMO Testing in Agricultural Crops and Plant-Derived Products, ASEAN Food J., vol. 15, pp. 1-25 (Year: 2008).*
Kruger, N.J., The Bradford Method for Protein Quantitation, Meth. Mol. Biol., vol. 32, pp. 9-15 (Year: 1994).*
Lipp, M. et al., IUPAC Collaborative Trial Study of a Method to Detect Genetically Modified Soy Beans and Maize in Dried Powder, J. AOAC Int., vol. 82, pp. 923-928 (Year: 1999).*
Christianson, J. et al., Detecting and Quantifying the Adventitious Presence of Transgenic Seeds in Safflower, Carthamus tinctorius L., J. Agric. Food Chem., vol. 56, pp. 5506-5513 (Year: 2008).*

(Continued)

*Primary Examiner* — Teresa E Strzelecka (74) *Attorney, Agent, or Firm* — Bereskin & Parr LLP/S.E.N.C.R.L., s.r.l.; Patricia Folkins (57) ABSTRACT

The present application relates to the detection of material from genetically engineered Genetically Modified Organisms (GMO) using a panel of GMO proteins and GMO gene elements. In particular, the present application discloses an improved method for detecting the presence or absence of a panel of GMO proteins and gene elements in a sample.

18 Claims, 2 Drawing Sheets

(56) References Cited

OTHER PUBLICATIONS

Kamata, N. et al., Comparison of pH and Ionic Strength Dependence of Interaction between Monoconal Antibodies and Bovine beta-Lactoglobulin, Biosci. Biotech. Biochem., vol. 60, pp. 25-29 (Year: 1996).*

Santiago-Felipe S., et al. "Recombinase polymerase and enzyme-linked immuonosorbent assay as a amplification-detection strategy for food analysis", Analytica Chimica Acta vol. 811 (2014), 81-87.

Jasbeer, K., et al, "Application of DNA and Immunoassay Analytical Methods for GMO Testing in Agricultural Crops and Plant-Derived Products", ASEAN Food Journal 15 (1): 1-25 (2008).

Novak, Petra Kralj et al., "GMOtrack: Generator of Cost-Effective GMO Testing Strategies", Journal of AOAC International, vol. 92, No. 6, 2009, 1739-1746.

Holst-Jensen, Arne, "Testing for genetically modified organisms (GMOs): Past, Present and future perspectives", Biotechnology Advances 27 (2009), 1071-1082.

Chernysheva, O.N., et al., "Analytical methods for control of foodstuffs made from bioengineered plants", Voprosy Pitaniia (2003) vol. 82, No. 3, 53-60 (English abstract only).

International Search Report and Written Opinion of corresponding PCT application No. PCT/CA2017/050210 completed May 23, 2017.

Training Course on "The Analysis of Food Samples for the Presence of Genetically Modified Organisms", User Manual, Luxembourg: Office for Official Publications of the European Communites, Querci, Maddalena, et al. Eds., Catalogue Number: LB-X1-06-051-EN-C, Edition 2006.

"Modern Techniques for Food Authentication", Chapters 12 and 13, Sun, Da-Wen Ed.,Elsevier (2008).

BIORAD, "Biotechnology Explorer GMO Investigator Kit", Catalog #166-2500EDU, 2015.

Spiegelhalter, F. et al., "Detection of Genetically Modified Food Products in a Commercial Laboratory", Journal of Food Science, vol. 66, Issue 5, Jun. 2001, p. 634-640.

De Leo, Federica et al., "Traceability and Detection of Genetically Modified Organisms in the Labelling of Food Production Chain. UE Directives and Molecular Approaches", 9th ICABR International Conference on Agricultural Biotechnology: Ten Years Later, Jul. 6-10, 2005, Ravello, Italy.

BIO-RAD, "Biotechnology Explorer GMO Investigator Kit: A Quantitative Real-Time PCT Extension" (2012).

GVO Screening Kits, Eurofins, Genescan, advertisement, Apr. 17, 2015.

R-Biopharm, SureFood GMO Screen 35S + NOS+FMV, advertisement, accessed Dec. 15, 2015.

ThermoFisher Scientific, TaqMan GMO Maize 35S Detection Kit, Catalog Number: 4327690, 2015.

Fraiture, Marie-Alice et al., "Current and New Approaches in GMO Detection: Challenges and Solutions", BioMed Research International, vol. 2015, Article ID 392872, p. 1-22.

Cox, Karen L. et al., "Immunoassay Methods", Assay Guidance Manual. p. 1-39 (2012).

Stephan, Oliver et al., "Development of a Real-Time PCT and a Sandwich ELISA for Detection of Potentially Allergenic Trace Amounts of Peanut (Arachis hyogaea) in Processed Foods", Journal of Agric. Food Chemistry, 2004, 52, p. 3754-3760.

Viljoen, Chris et al., "Overview of Available Detection Methods, including Validated Methods", Technical Tools and Guidance for the Detection and Identification of LMOs, accessed Dec. 15, 2015.

Ahmed, Farid E. "Detection of genetically modified organisms in food", TRENDS in Biotechnology, vol. 20, No. 5, May 2002, p. 215-223.

Miraglia, M., et al., "Detection and traceability of genetically modified organisms in the food production chain", Food and Chemical Toxicology, 42, 2004, 1157-1180.

Malou, Nada et al., "Immuno-PCR: a promising ultrasensitive diagnositc method to detect antigens and antibodies", Trends in Microbology, Jun. 2011, vol. 19, No. 6, p. 295-301.

Guertler, Patrick et al., "Sensitive and highly specific quantitative real-time PCT and ELISA for recording a potential transfer of novel DNA and Cry1Ab from feed into bovine milk", Anal Bioanal Chem (2009), 393, p. 1629-1638.

* cited by examiner

METHODS FOR DETECTING GENETICALLY MODIFIED ORGANISMS (GMO)

RELATED APPLICATIONS

This application is a national stage of co-pending International Application No. PCT/CA2017/050210, filed on Feb. 17, 2017, which claims the benefit of priority of U.S. Provisional Patent Application No. 62/297,386 filed Feb. 19, 2016, the contents of both of which are incorporated by reference herein in their entirety.

FIELD

The present application relates to improved methods for the detection of genetically engineered Genetically Modified Organisms (GMO) using a panel of GMO proteins and GMO gene elements. In particular, the present application discloses a method for detecting the presence or absence of GMO material in a sample that provides more accurate and/or useful results than current GMO testing methods.

BACKGROUND

A Genetically Modified Organism (GMO) is created through the modification of the native genes of an organism using recombinant DNA technology. This modification may express a gene that is not native to the organism or modify endogenous genes. The resulting protein encoded by the modified gene will confer a particular trait or characteristic of the non-native gene. Typically, the technology has been used to engineer resistance to abiotic stresses, such as drought and extreme temperature or salinity and biotic stresses, such as insects and pathogens. The technology has also been used to improve the nutritional content of plants which has seen wide applications in the developing world. Further, new-generation GMO crops are being developed for the introduction of recombinant medicines and industrial products, including monoclonal antibodies, vaccines, plastics and biofuels [1-3].

The use of GMO crops has steadily increased globally over the past two decades [4]. The principle GMO crops grown are soybean and maize with cotton, canola and rice also on the rise. GMO crops are non-uniformly distributed in the bulk food, thus there are variances in genetically modified content across samples.

Some nations, such as the European Union, have placed stringent restrictions on GMO content in food. Consumers also desire to know whether or not they are consuming foods that contain GMO material. Therefore sampling strategies for the quantitative detection of GMO content are needed. Consequences of errors in sampling procedures, and hence quantitative assessment of the GMO content in food samples, can lead to false negative and false positives. This can result in mislabeled products entering the marketplace. Therefore, reliable sampling procedures or methods are needed.

SUMMARY

The number of Genetically Modified Organism (GMO) food and feed products generated, authorized and marketed globally has increased significantly in the past two decades. Specifically, combinations of different GMO markers (proteins and gene elements) may be shared by one plant or food sample. Screening for particular combinations of GMO markers would therefore more accurately determine if a sample contains GMO material. In addition, many of the same food products tested vary greatly in their % GMO content as a result of the degree of processing. Thus it is advantageous to assess both GMO gene elements and GMO proteins in case one is absent or degraded due to processing.

In one aspect, the methods described herein include the use of PCR amplification for detecting GMO gene elements and an immunoassay for the detection of GMO proteins in a sample. Optionally, the methods may also include the use of a DNA and/or protein detection step in order to confirm the presence or absence of DNA and/or protein in the sample. In one embodiment, the methods described herein allow for the level of GMO proteins in the sample to be detected, such as by the use of purified GMO protein standards. In one embodiment, the use of specific GMO protein standards, and not GMO crops or plant materials known to be genetically modified, allows for the improved detection and/or quantification of the levels of GMO material, especially in finished food and natural health products where GMO plant species of origin are often unknown.

Accordingly, in one embodiment, there is provided a method for testing a sample for the presence or absence of Genetically Modified Organism (GMO) material comprising detecting the presence or absence of one or more GMO gene elements selected from P35S promoter from cauliflower mosaic virus (CaMV), NOS terminator from *A. tumefaciens* and P34S promoter from figwort mosaic virus (FMV) in the sample and detecting the presence or absence of one or more GMO proteins selected from Cry1Ab, Cry2Ab, Cry34Ab1, Cry1Ac, Cry3Bb, Cry1F, VIP3a, NPTII, PMI, CP4 EPSPS and PAT. In one embodiment, the method comprise detecting at least two GMO gene elements selected from P35S promoter from CaMV, NOS terminator from *A. tumefaciens* and P34S promoter from FMV in the sample and detecting at least two, three, four, five, six, seven, eight, nine or ten GMO proteins selected from Cry1Ab, Cry2Ab, Cry34Ab1, Cry1Ac, Cry3Bb, Cry1F, VIP3a, NPTII, PMI, CP4 EPSPS and PAT in the sample.

In one embodiment, the present application includes a method for testing a sample for the presence or absence of Genetically Modified Organism (GMO) material comprising:
  detecting the presence or absence of GMO gene elements in the sample wherein the GMO gene elements comprise P35S promoter from cauliflower mosaic virus (CaMV), NOS terminator from *A. tumefaciens* and P34S promoter from figwort mosaic virus (FMV); and
  detecting the presence or absence of GMO proteins in the sample wherein the GMO proteins comprise Cry1Ab, Cry2Ab, Cry34Ab1, Cry1Ac, Cry3Bb, Cry1F, VIP3a, NPTII, PMI, CP4 EPSPS and PAT;
  wherein the presence or absence for the GMO gene elements in the sample are detected using PCR amplification and wherein the presence or absence of the GMO proteins in the sample are detected using an immunoassay.

In one embodiment, the PCR amplification comprises quantitative PCR or digital PCR, optionally droplet digital PCR (ddPCR). In one embodiment, if the sample comprises a processed food or is suspected of having been degraded, the method comprises using digital PCR and preferably ddPCR for the detection of GMO gene elements.

In one embodiment, the immunoassay is an ELISA assay. The immunoassay may be used to detect a level of one or more of the GMO proteins in the sample. In one embodiment, the immunoassay detects a relative amount of one or more of the GMO proteins in the sample, optionally (w/w) or parts per billion (ppb). In one embodiment, the method comprises detecting a plurality of protein standards, such as a dilution series of an isolated protein standard, using the immunoassay to obtain a standard curve. In a preferred embodiment, the immunoassay detects a level of Cry1Ab, Cry2Ab, Cry34Ab1, Cry1Ac, Cry3Bb, Cry1F, VIP3a, NPTII, PMI, CP4 EPSPS and PAT in the sample.

In one embodiment, the method comprises detecting a level of total protein in the sample, optionally using a Bradford assay and/or SDS-PAGE.

In one embodiment, the method comprises subjecting the sample to a protein extraction step prior to detecting the presence or absence of GMO proteins and/or total protein in the sample. In one embodiment, the method comprises subjecting the sample to a DNA extraction step prior to detecting the presence or absence of GMO gene elements in the sample. In one embodiment, the method comprises homogenizing sample, such as by grinding or agitating the sample, prior to detecting the presence or absence of protein and/or DNA in the sample.

In one embodiment there is provided a method for testing a sample for the presence or absence of GMO material comprising:
(i) homogenizing the sample by one of:
  (a) if the sample is a solid, grinding the solid to a powder,
  (b) if the sample is a semi-solid, freezing the sample and grinding frozen sample to a powder, and
  (c) if the sample is a liquid, agitating the sample if necessary for homogenization;
(ii) extracting DNA from a portion of the sample in (i);
(iii) extracting protein from a portion of the sample in (i);
(iv) confirming a presence or absence of DNA in the extract obtained in (ii);
(v) confirming a presence or absence of protein in the extract obtained in (iii);
(vi) performing a PCR amplification on the extract obtained in (ii) that contains DNA to detect the presence or absence of GMO gene elements in the extract, wherein the GMO gene elements comprise P35S promoter from cauliflower mosaic virus (CaMV), NOS terminator from *A. tumefaciens* and P34S promoter from figwort mosaic virus (FMV); and
(vii) performing an immunoassay on the extract obtained in (iii) that contains protein to detect the presence or absence of GMO proteins in the extract, wherein the GMO proteins comprise Cry1Ab, Cry2Ab, Cry34Ab1, Cry1Ac, Cry3Bb, Cry1F, VIP3a, NPTII, PMI, CP4 EPSPS and PAT.

In one embodiment, a separate PCR amplification is performed for each GMO gene element. Alternatively or in addition, a separate immunoassay is performed for each GMO protein. Confirming the presence or absence of DNA in the extract may include detecting a level of DNA in the sample. Confirming the presence or absence of protein in the extract may include detecting a level of protein in the extract. Methods suitable for detecting total protein in the sample include using a Bradford assay or SDS-PAGE (e.g. using Coomassie blue or silver nitrate staining) or other techniques known in the art.

In one embodiment, detecting the presence of at least one GMO gene element and/or GMO protein in a sample as described herein allows for the identification of the sample as comprising GMO material. This identification may then be used to label a product, from which a representative sample was obtained and tested, as comprising a GMO material or being free of GMO material or using other terms indicative of the presence, absence or level of GMO materials. In one embodiment, a plurality of samples representative of a product and/or representative of ingredients used to prepare the product are tested for the presence or absence of GMO materials as described herein. In one embodiment, the sample comprises GMO material from a GMO species of unknown origin. In one embodiment, the sample comprises GMO material from a GMO species of unknown origin and the method comprises detecting a plurality of GMO protein standards in order to detect a level of GMO protein in the sample.

Also included in the present application are kits for performing the methods defined herein.

Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

BRIEF DESCRIPTION OF THE DRAWINGS

The application will be described in greater detail with reference to the accompanying drawings in which.

DETAILED DESCRIPTION

I. Definitions

Unless otherwise indicated, the definitions and embodiments described in this and other sections are intended to be applicable to all embodiments and aspects of the present application herein described for which they are suitable as would be understood by a person skilled in the art.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

As used in this application, the singular forms "a", "an" and "the" include plural references unless the content clearly dictates otherwise. For example, an embodiment including "a sample" should be understood to present certain aspects with one sample or two or more additional samples.

In embodiments comprising an "additional" or "second" sample, the second component as used herein is different from the other components or first component. A "third" component is different from the other, first, and second components, and further enumerated or "additional" components are similarly different.

The term "and/or" as used herein means that the listed items are present, or used, individually or in combination. In effect, this term means that "at least one of" or "one or more" of the listed items is used or present.

The terms "Genetically Modified Organism" or "GMO" as used herein refers to genetically engineered organisms in which the genetic material (DNA) has been altered to express non-native traits which do not occur naturally by mating or natural recombination. Examples of non-native traits include, but are not limited to, herbicide tolerance, insect resistance, abiotic and biotic stress resistance.

The term "transformation event" as used herein is defined as an event in which at least one gene from at least one organism is transferred to another organism producing a non-native trait in the transformed organism, which is then passed to all subsequent identical clones.

The term "processed food" refers to fresh crop or plant material that has been artificially processed through air-drying, dehydration, refrigeration, cooking, heating and/or preservation with or without the use of chemical agents.

The term "sample" as used herein refers to a fraction of any material that one wishes to test for the presence or absence of GMO material. Examples of samples include, but are not limited to, food including processed food, plants or plant materials, nutritional supplements, Natural Health Products (NHPs), and environmental samples (e.g. water or soil samples) suspected of containing GMO materials. In one embodiment, the sample is sample that is representative of a product, batch or crop. For example, in one embodiment the sample is representative of a batch of processed food that is manufactured in the same facility and/or using the same ingredients. In one embodiment, the sample contains, or is suspected of containing, a GMO from an unknown species.

As used herein "agitating" refers to any method known in the art for homogenizing a sample and includes mixing, shaking, or stirring.

As used herein "immunoassay" refers to a method of detecting a protein target using a specific binding agent such as an antibody or antibody fragment. In one embodiment, the specific binding agent comprises a detectable label, such as an isotope, fluorescent label or enzyme. In one embodiment, the immunoassay produces a detectable color change in the presence of a protein target. In one embodiment, the immunoassay is an ELISA assay. Antibodies and/or ELISA assay kits for the detection of GMO proteins such as Cry1Ab, Cry2Ab, Cry34Ab1, Cry1Ac, Cry3Bb, Cry1F, VIP3a, NPTII, PMI, CP4 EPSPS and PAT are commercially available.

The terms "ELISA assay" or ELISA assay kit" refer to an enzyme-linked immunosorbent assay (ELISA) that uses antibodies and color change to identify a substance of interest, such as a protein selected from Cry1Ab, Cry2Ab, Cry34Ab1, Cry1Ac, Cry3Bb, Cry1F, VIP3a, NPTII, PMI, CP4 EPSPS and PAT. In one embodiment, the ELISA is a sandwich ELISA. In one embodiment, antigens from a sample to be screened or tested are attached to a surface and a further specific antibody is applied over the surface so it can bind to the antigen. The antibody is linked to an enzyme and a substance containing the enzyme's substrate is added. The subsequent colorimetric reaction turnover produces a detectable signal, i.e. the absorbance of a colored product. Standard ELISA methods are known in the art.

The term "PCR" or "polymerase chain reaction" as used herein refers to the use of template DNA, nucleotides (dNTPS) and primers that bind to the template DNA to selectively amplify a target sequence. PCR is a technology that can be used to amplify a single copy or few copies of a DNA sequence by several orders of magnitude, generating thousands to millions of copies of the DNA sequence. Standard PCR methods are known in the art. PCR amplification and the detection of an amplified target sequence can be used to detect specific GMO gene elements in a sample. Quantitative PCR methods such as real time PCR may be used to determine the absolute or relative amounts of a known sequence in a sample. Digital PCR methods may also be used for detecting and/or quantifying target sequences in a sample.

The term "standard curve" as used herein refers to a set of standards with known properties, such as concentration, which are tested and used to determine the same property for one or more unknown samples, such as by interpolation on a graph.

The term "w/w" as used herein refers to the weight of GMO protein per gram of sample (for e.g., ng of GMO protein per gram of sample, or ppb).

II. A Method of the Application

Combinations of GMO proteins and GMO gene elements may be shared by one plant or food sample. Screening for particular combinations of GMO proteins and GMO gene elements would more accurately determine if a sample contains GMO. In addition, many of the same food products tested vary greatly in their % GMO content as a result of the degree of food processing. Thus it is advantageous to assess both GMO gene elements and GMO proteins in case one is absent or degraded due to the degree of processing. Furthermore, the complementary use of PCR amplification and an immunoassay for detecting specific GMO gene elements and GMO proteins as described herein provides a comprehensive and reliable method for detecting GMO materials.

Accordingly the present application includes a method for testing a sample for the presence or absence of GMO material. In one embedment, the method comprises:
  i) detecting the presence or absence of GMO gene elements in the sample for wherein the GMO gene elements comprise P35S promoter from cauliflower mosaic virus (CaMV), NOS terminator from *A. tumefaciens* and P34S promoter from figwort mosaic virus (FMV); and
  ii) detecting the presence or absence of GMO proteins in the sample wherein the GMO proteins comprise Cry1Ab, Cry2Ab, Cry34Ab1, Cry1Ac, Cry3Bb, Cry1F, VIP3a, NPTII, PMI, CP4 EPSPS and PAT;
  wherein the presence or absence for the GMO gene elements in the sample are detected using PCR amplification and wherein the presence or absence of the GMO proteins in the sample are detected using an immunoassay.

In one embodiment, detecting the presence of at least one GMO gene element or GMO protein in the sample indicates the presence of GMO material in the sample.

In an embodiment, the sample comprises a plant or parts thereof. In an embodiment, plant may refer to plant tissues which are selected from root, leaf, stem, flower, fruit and seed, and mixtures thereof. In one embodiment, the plant is an agricultural plant. In one embodiment, the sample comprises a food or feed material, optionally a plant. In one embodiment, the sample is any food that is to be ingested by an animal, including livestock, humans and companion animals. In an embodiment, the food is selected from fresh produce, fresh food, frozen food and/or processed food. In one embodiment, the sample comprises a supplement or other ingestible material, such as a nutritional supplement, or a Natural Health Product (NHP).

In an embodiment, the sample is a solid, liquid or semi-solid (e.g., gel). In one embodiment, the sample comprises a food or feed material that has been processed such as to degrade the presence of one or more GMO biomarkers such as GMO proteins. In one embodiment, the sample comprises a processed food and the method comprises detecting GMO gene elements in the sample. In one embodiment, the sample comprises, or is suspected of comprising, GMO material from an unknown species.

In one embodiment, the methods described herein include testing a sample or samples that are representative of a product such as type of plant (e.g. a specific crop from a particular source) or a type of food or food product (such as a specific processed food or batch of processed food). Testing a sample or samples that are representative of a product to determine the presence or absence of GMO material can be used to identify or label the product with respect to the presence or absence of GMO material.

In an embodiment, the method of the present application comprises a protein extraction step. In one embodiment, the method comprises a protein extraction step prior to detecting GMO proteins in an immunoassay, optionally in an ELISA. The addition of a protein extraction step separates soluble GMO proteins from other components of complex food and supplement matrices. In another embodiment, the sample or extracted protein is then run on SDS-PAGE to confirm the presence of total protein prior to running the immunoassay testing for GMO proteins. Samples containing no protein that provide a positive result for GMO proteins are ruled as false positives. Such false positive are common, for example, with dietary supplement products and other samples containing iron.

In one embodiment, the method comprises subjecting the sample to a protein extraction step prior to detecting the presence or absence of GMO proteins in the sample and/or detecting the presence or absence of total protein in the sample. Various methods of extracting proteins for subsequent detection in immunoassays are known in the art. In one embodiment, the protein extraction step comprises grinding and/or homogenizing the sample followed by extraction using an extraction buffer. In one embodiment, the extraction buffer is Tris-HCl.

The presence or absence of total protein in the sample or extract can be determined using methods known in art such as a Bradford assay or SDS-PAGE. In one embodiment, the detecting the presence of absence of total protein includes detecting a level of total protein in the sample or extract. The level or concentration of protein in the sample or extract can then be used to adjust the amount of sample added to the immunoassay for the detection of GMO proteins.

In one embodiment, the methods described herein include detecting the presence or absence of one or more GMO proteins in a sample or extract thereof using an immunoassay. The immunoassay may also be used to detect a level of the one or more of the GMO proteins in the sample. In one embodiment, the immunoassay detects a relative amount (w/w) of one or more of the GMO proteins in the sample. In one embodiment, the immunoassay quantifies the relative amount (w/w) of at least 2, 3, 4, 5, 6, 7, 8, 9, 10 or 11 GMO proteins selected from Cry1Ab, Cry2Ab, Cry34Ab1, Cry1Ac, Cry3Bb, Cry1F, VIP3a, NPTII, PMI, CP4 EPSPS and PAT in the sample.

As set out in Example 3, the use of purified GMO protein standards is advantageous for identifying GMO material relative to the use of single species GMO standards. Accordingly, in one embodiment the method comprises detecting a plurality of protein standards using the immunoassay to obtain a standard curve. The standard curve may then be used to determine the level of GMO proteins in the sample (s). In one embodiment, standard solutions of GMO proteins such as Cry1Ab, Cry2Ab, Cry34Ab1, Cry1Ac, Cry3Bb, Cry1F, VIP3a, NPTII, PMI, CP4 EPSPS and/or PAT proteins may be generated by diluting commercially available recombinant versions of those proteins. In one embodiment, the plurality of protein standards comprises a dilution series of at least 2, 3, 4, 5, 6, 7, 8, 9, or 10 dilutions for each GMO protein. In one embodiment, the plurality of protein standards comprises at least 5 dilutions for each GMO protein. In one embodiment, the plurality of protein standards comprises 8 dilutions for each GMO protein.

In one embodiment, the protein standards and the presence or absence of the GMO protein(s) in the sample are detected concurrently. For example, in one embodiment, the protein standards and the presence or absence of GMO protein in one or more samples are tested on the same plate, such as 96 well microtiter plate suitable for use in immunoassays.

In one embodiment, the immunoassay is an ELISA, optionally a sandwich ELISA. In an embodiment, incubation with the capture antibody is separated from incubation with the detection antibody in the ELISA. Separation of the incubation of both the capture and detection antibodies decreased the false positives due to less interference from substances in the initial incubation with the capture antibody.

Using purified GMO protein standards in the ELISA is broadly applicable to several supplement and food matrices opposed to the species specific % GMO material standards that come with commercial ELISA kits. Accordingly, in an embodiment, the ELISA comprises purified protein standards to obtain w/w of the GMO protein in sample. The added purified protein standards provide w/w results for each of the 11 GMO proteins as disclosed in the present application. Quantitative w/w data for each specific GMO protein in ng/g (ppb) is disclosed in the present application instead of % GMO material as disclosed in the original kit standards or in the prior art.

The immunoassays described herein for the detection of GMO proteins may be used to detect low levels of GMO proteins in a sample. In an embodiment, the detection limit of GMO protein using the methods of the application is as low as 4 ppb. In another embodiment, the detection limit is as high as 320 ppb. In an embodiment, the detection limit is from about 4 ppb to about 320 ppb. In another embodiment, the detection limit is from about 5 ppb to about 240 ppb. In one embodiment, the immunoassay has a detection limit for of at least 5 ppb, at least 10 ppb, at least 20 ppb, at least 50 ppb, at least 100 ppb or at least 200 ppb for one or more of the GMO proteins. In one embodiment, the method disclosed in the present application is useful relative to other methods because consumers can use the quantitative w/w result to determine the exact GMO protein content that is present in, for example, a food product, in addition to alerting consumers to the presence or absence of GMO material.

In one embodiment, the methods described herein include detecting the presence or absence of GMO gene elements in the sample. In one embodiment, the sample, or extract thereof, is tested for the presence of absence of total DNA prior to performing a PCR amplification to detect GMO gene elements. Samples containing no DNA that provide a positive result for GMO gene elements are ruled as false positives.

Different methods known in the art for amplifying target nucleotide sequences using PCR may be used to detect the presence or absence of the GMO gene elements as described herein. Optionally, quantitative PCR methods may be used that provide a measure of a level of a target GMO gene element in the sample. In one embodiment, the methods described herein use digital PCR methods for amplifying and detecting target GMO gene elements. As demonstrated in the Example 4, the use of digital PCR methods may improve the accuracy of detecting GMO gene elements relative to standard qRT-PCR.

In an embodiment, the PCR amplification is performed using droplet digital (dd)PCR. The addition of a GMO-gene testing platform, specifically the addition of PCR to screen for common GMO gene elements as a complementary process to ELISA, helps to confirm the accuracy of the ELISA results and provides a more comprehensive approach to the testing of samples for GMO content. In another embodiment, samples containing very low yields of DNA (5-10 ng) are tested using the highly sensitive digital PCR techniques such as ddPCR technique which is well known in the art.

Each protein and gene element includes any portion or analog of sequences known in the art to selectively identify the indicated gene and protein. The tools, including purified protein standards, antigens and antibodies for ELISA and primers and reagents for PCR are available from commercial sources and kits. Tools for ELISA which include purified protein standards can also be synthesized using known protein expression and purification methods in the art. Similarly, procedures for generating, purifying and modifying antibodies for uses as antigen-specific probes are well-known in the art. In addition, primers for PCR can be synthesized using DNA synthesis and purification methods known in the art.

Figure 1:
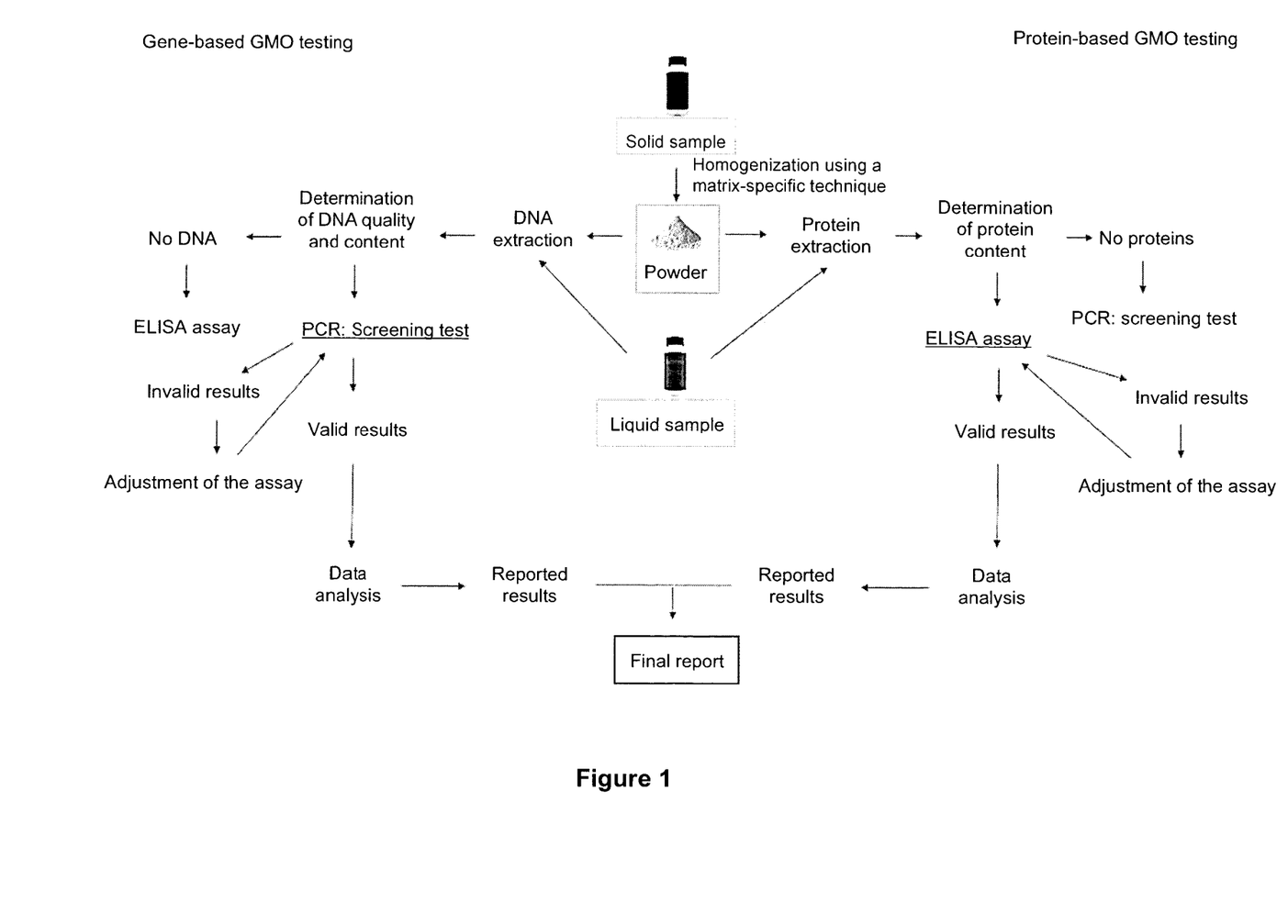
FIG. 1 shows a flow chart that incorporates embodiments of the method of the application.

An embodiment of the method of the application for testing a sample for the presence or absence of GMO material is shown in FIG. 1. In one embodiment, the method comprises:
(i) homogenizing the sample by one of:
  (a) if the sample is a solid, grinding the solid to a powder,
  (b) if the sample is a semi-solid, freezing the sample and grinding frozen sample to a powder, and
  (c) if the sample is a liquid, agitating the sample if necessary for homogenization;
(ii) extracting DNA from a portion of the sample in (i); and
(iii) extracting protein from a portion of the sample in (i).
In one embodiment, the method further comprises:
(iv) confirming a presence or absence of DNA in the extract obtained in (ii); and/or
(v) confirming a presence or absence of protein in the extract obtained in (iii).
In one embodiment, the method further comprises:
(vi) performing a PCR amplification on the extract obtained in (ii) that contains DNA to detect the presence or absence of GMO gene elements in the extract, wherein the GMO gene elements comprise P35S promoter from cauliflower mosaic virus (CaMV), NOS terminator from *A. tumefaciens* and P34S promoter from figwort mosaic virus (FMV); and/or
(vii) performing an immunoassay on the extract obtained in (iii) that contains protein to detect the presence or absence of GMO proteins in the extract, wherein the GMO proteins comprise Cry1Ab, Cry2Ab, Cry34Ab1, Cry1Ac, Cry3Bb, Cry1F, VIP3a, NPTII, PMI, CP4 EPSPS and PAT.

Various methods or techniques described herein as well as methods or techniques known in the art may be used, either alone or in combination, for performing the PCR amplification to detect the presence of GMO gene elements and/or performing the immunoassay to detect the presence of absence of GMP proteins.

In one embodiment, a separate PCR amplification is performed for each GMO gene element. In one embodiment, a separate immunoassay is performed for each GMO protein. In one embodiment, confirming the presence or absence of DNA in the extract comprises detecting a level of DNA in the extract. In one embodiment, confirming the presence or absence of protein in the extract comprises detecting a level of protein in the extract. In an embodiment, confirming the presence of protein in the extract obtained in step (iii) is performed using SDS-PAGE or using a Bradford assay.

In an embodiment, the freezing of the semi-solid sample is performed using dry ice, a dry ice/ethanol slurry or liquid nitrogen.

In an embodiment, the immunoassay quantifies a relative amount (w/w) of the GMO proteins in the sample and the method comprises detecting a plurality of protein standards using the immunoassay to obtain a standard curve as described herein.

In an embodiment, if valid results are not obtained in the PCR and/or immunoassay of steps (vi) and/or (vii) then adjustments to the assay are made to obtain valid results. Valid results may not be obtained if, for example, the levels of GMO protein and/or GMO gene elements are significantly higher or lower than expected, or suspected to be falsely positive or negative based on what is known about the plant species origin of a given sample.

In one embodiment if valid results are not obtained in the PCR amplification of step (vi) the method comprises:
  adjusting the extraction of DNA from the sample in step (ii) or adjusting the PCR amplification of step (vi); and
  retesting the sample for the presence or absence of the GMO gene elements.

In one embodiment, adjusting the extraction of DNA from the sample comprises extracting DNA from >100 mg of sample starting material, eluting DNA in a smaller volume of water to provide a more concentrated sample, and/or performing a second DNA elution to provide a better yield of total DNA and other such techniques.

In one embodiment, if valid results are not obtained in the immunoassay of steps (vii) the method comprises:
  adjusting the extraction of protein from the sample in step (iii) or adjusting the immunoassay of step (vii); and
  retesting the sample for the presence or absence of the GMO proteins.

In an embodiment, the adjustments to the immunoassay may include, but are not limited to, reconfirming and adjusting the pH to an optimal range, optionally a range of about 6 to about 8, removing heavy metals such as iron through standard dialysis techniques and other such techniques.

In one embodiment, the methods described herein may further include generating a summary indicative of the presence or absence of GMO material in the sample based on the results from steps (iv), (v), (vi) and/or (vii).

In an embodiment, the results from steps (iv), (v), (vi) and (vii) are analyzed and a report is provided regarding the presence or absence of GMO material in the sample. In an embodiment, the results are reported as shown in Table 6, depending on the results of each of steps (iv), (v), (vi) and (vii).

In an embodiment, the results from the methods described herein for testing a sample for the presence of absence of GMO material are used to label a sample, such as a food product, with information pertaining to its GMO content. For example, the method is used to confirm that a sample, such as a food product is absent of GMO material, is GMO-free, or other relevant terms guided by regulatory bodies.

In one embodiment the sample is representative of a food or food product and the method further comprises labelling the food or food product based on the presence or absence of GMO material in the sample. In one embodiment, the method comprises testing a plurality of samples that are representative of the food or food product for which representative samples were tested. In one embodiment, if the sample(s) are absent of GMO material the food or food product or other material is identified and/or labeled as GMO-free, or identified or labeled using other relevant terms guided by regulatory bodies.

In an embodiment, the sample is representative of one or more ingredients used to prepare a food product or other material. In a further embodiment, each of the ingredients, their raw materials and/or process chemicals used to prepare the food product are tested for the presence or absence of GMO material using method as described herein. In another embodiment, the ingredients, their raw materials and/or process chemicals include the feed for the microbes that produce enzymes in the product. In a further embodiment, the results from tests performed on the food products and each of the ingredients, their raw materials and/or process chemicals used to prepare the food product, are used to identify or label the food products with information pertaining to its GMO content. For example, the method is used to confirm that representative sample(s), and by association a food product, including all ingredients, their raw materials and/or process chemicals used to prepare the food product, are absent of GMO material, is GMO-free or any other such term set by regulatory bodies. Therefore, in an embodiment, the methods described herein may be are used to confirm that no GMO materials were used anywhere in the manufacture of the product.

Figure 2:
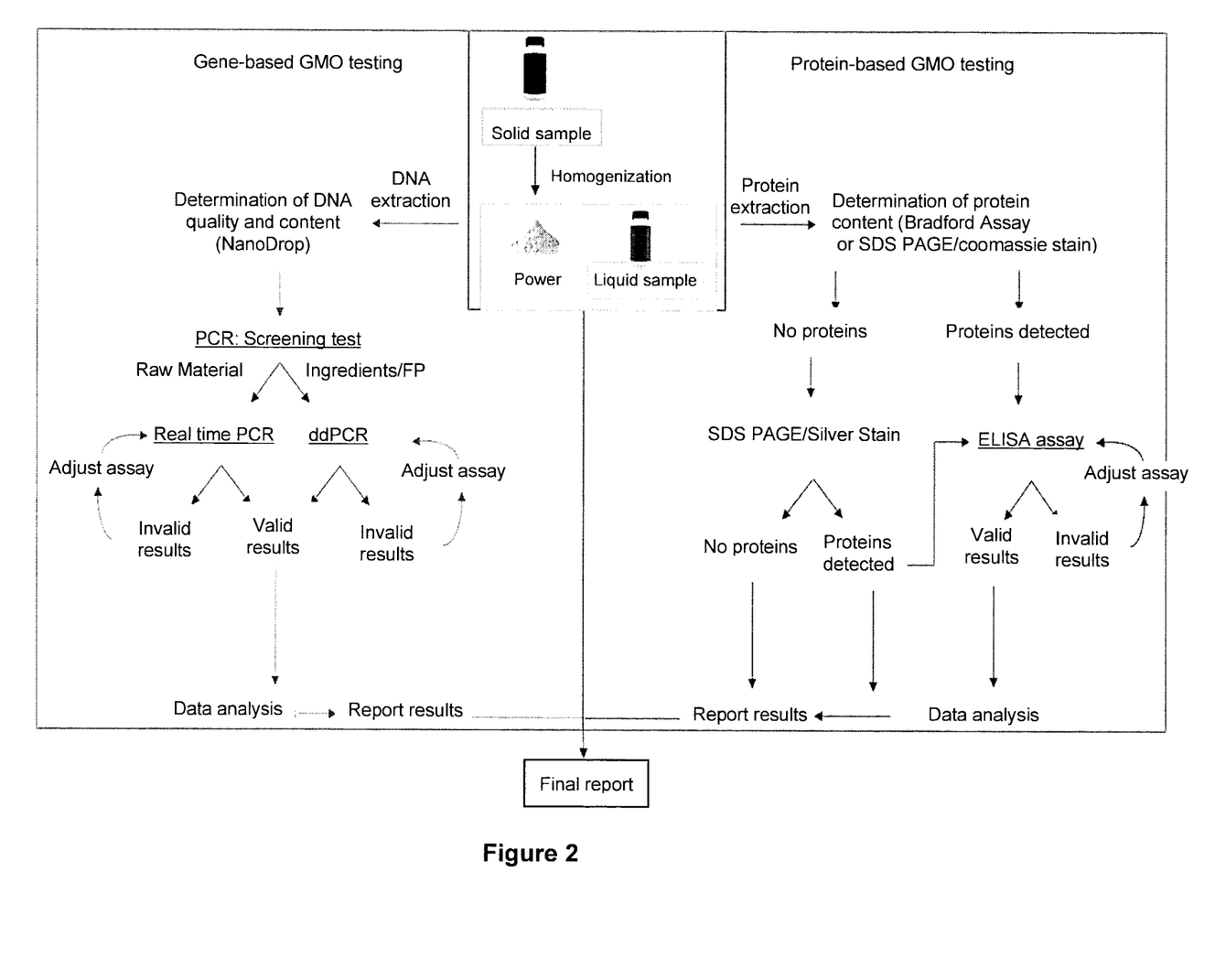
FIG. 2 shows flow chart that incorporates embodiments of the method of the application including the use of digital PCR.

FIG. 2 shows an exemplary method for testing a sample for the presence or absence of GMO material as described herein. First, attempts to extract both protein and DNA from homogenized samples are made. Products tested may vary significantly in their content and degree of processing, thus it is advantageous to assess both GMO genes and proteins in case one is absent or degraded. After extraction, the presence or absence of DNA and protein in the sample is confirmed before proceeding. If DNA is present in the sample, PCR screening can be conducted to detect GMO gene elements in the sample. GMO gene elements may be detected using conventional RT-PCR for raw materials (e.g. plants, crops, fresh foods) and ddPCR for processed products or ingredients (e.g. baked goods). Invalid results may be subject to adjustment of the PCR amplification method to obtain valid results, for example DNA cleaning to remove PCR inhibitors. If protein is not detected in the sample, no further immunoassay testing is required and results may be reported. If protein is present an immunoassay is conducted to detect GMO proteins in the sample. Invalid results may be subject to adjustment of the immunoassay to obtain valid results. Results from PCR and ELISA tests are compiled into a final report. If valid results cannot be obtained using either method, further testing of sub-components and/or raw materials may be required to assess GMO status. Samples may optionally be prepared and tested for GMO genet elements and/or GMO proteins in duplicate or triplicate.

The present application also includes kits for performing a method of the application.

EXAMPLES

The following non-limiting examples are illustrative of the present application:

Example 1

Methods and Conditions for Extraction of DNA and Proteins From Test Sample

Sample Processing

Prior to protein or DNA extraction, 10 g of solid test sample (or non-GMO soybean and corn control) was weighed, ground into a fine powder within a disposable grinding chamber using a Tube Mill Control grinder, and then stored at 4° C. Test samples composed of semi-solid matrices were freeze-dried in dry ice prior to grinding, while liquids did not require this processing step.

DNA Extraction

Control (non-GMO corn or soybeans) and test sample DNA was extracted from 100 mg of homogenized sample powder (or liquid) using the kit manufacturer's protocol. Sterile $H_2O$ served as a negative process control. DNA extraction may be performed in duplicate resulting in duplicate samples that are tested for GMO gene elements as described herein.

DNA Cleaning

Samples determined to contain PCR inhibitors were cleaned with DNeasy PowerClean Pro Cleanup kit from MoBio Laboratories Inc. Briefly, 100 µL of sample DNA, along with positive GMO soybean and corn control) and negative (sterile water) controls were cleaned for PCR following manufacturer's protocol.

Protein Extraction

Control (non-GMO corn or soybeans) and test sample protein was extracted from 1 g of sample powder in 8 mL of extraction buffer (75 mM Tris-HCl, pH 7.5). Samples were shaken for 20 min at room temperature (RT) and then centrifuged at 3,000×g for 20 min. The pH of the sample supernatants (working solutions) were checked and the pH was adjusted between 6.0 and 8.0, if necessary. Working solutions were stored at −20° C. Prior to running ELISA, samples were thawed to RT and then centrifuged for 2 min at 20,000×g. Protein presence in supernatant was confirmed with standard SDS-PAGE methods using either Coomassie blue or silver nitrate staining. Protein extraction may be performed in duplicate resulting in duplicate samples that are tested for GMO proteins as described herein.

Example 2

Methods and Conditions for the Amplification of DNA

Amplification of DNA and GMO Gene Screening Through Droplet Digital (dd) PCR

The quantity and quality of DNA was assessed using standard UV/VIS Spectroscopy. In a 96-well PCR plate, 50 ng of DNA from non-GMO controls and 100 ng of DNA from test samples was mixed with prepared master mixes for each of the common bioengineering gene elements (P35S, TNOS, and P34S) and plant DNA control according to the manufacturer's instructions. The dNTP mix included in the GMO screening kit was replaced with a dNTP mix without dUTP suitable for ddPCR. The method contains additional internal controls to distinguish if the original source of P35S, TNOS and P34S were from GMO/GE attempts or naturally occurring from Cauliflower Mosaic Virus (CaMV), *A. tumefaciens* or Figwort Mosaic Virus (FMV), respectively. All primer and probe sequences are proprietary to the manufacturer, and have been validated in food and feed according to ISO17025 guidelines. Next, the PCR plate with complete reaction mixes was put into a manual (QX200™ Droplet Generator) or automated droplet generator according to the manufacturer's instructions. Following droplet generation, the plate was placed in a Thermal Cycler to amplify the DNA using the conditions listed in Table 1.

Example 3

Methods and Conditions of Hybridization and Signal Detection

Droplet Reading, Results Analysis and Interpretation Using ddPCR

Droplets were read with the QX200™ Droplet Reader and then analyzed with QuantaSoft Program software according to the manufacturer's instructions. Separation in droplet fluorescence is indicative of positive PCR reactions, suggesting the presence of target DNA (bioengineering elements: P35S, TNOS, and P34S or plant control). Droplets which do not contain any of these elements do not fluoresce. The results for each sample were considered acceptable only if the droplet count for each well was above 10,000. All samples containing more than 5 copies of target gene per μL were classified as positive samples.

Example 4

Methods and Conditions for Performing ELISA Assays

All 11 ELISA's were performed according the assay manufacturer's protocols with some modifications. Briefly, 100 μL of sample protein working solution, negative control (non-GMO corn), purified protein standards or blank (extraction buffer) were plated in duplicate for 1-2 hour incubation (depending on the assay) with the primary (capture) antibody. ELISA plates were then washed 5 times using 200 μL/well of wash buffer (1× Phosphate Buffered Saline with Tween® 20: 8 mM $Na_2HPO_4$, 150 mM NaCl, 2 mM $KH_2PO_4$, 3 mM KCl, 0.05% Tween® 20, pH 7.4), and then blotted dry on clean paper towel. Further incubation steps with the secondary enzyme-conjugated antibody, colorimetric substrate, and stop solution were performed as described in the manufacturer's protocols. The optical density (OD) was measured on a plate reader at 450 nm. Results were considered valid if the OD of all points of the calibration curve were within the range of 0.25 to 2.0, the % CV of OD reading duplicates for all standards was ≤15%, and the % CV of OD reading duplicates for unknown samples was ≤20%. The weight (ng) of GMO protein per gram of sample was calculated by multiplying the obtained results (ng/mL) by the volume of extraction buffer (mL), and then dividing that number by the mass of the sample (g).

Example 4

Comparative Example Droplet Digital (dd) PCR Vs Industry Standard Real-Time qPCR The droplet digital (dd) PCR used for detecting GMO gene elements in the panel of GMO gene elements (p35S, TNOS and p34S) disclosed in the present application, produces more accurate results when testing complex food and supplement matrices than the industry standard real-time quantitative PCR (RT-qPCR). Table 2 illustrates that samples tested by qPCR had false positives for one or more GMO genes detected in the late PCR cycles (37-43).

Example 5

Comparative Example Using Purified GMO Protein Standards in Elisa Assays

Table 3 illustrates a comparative example of different transformation events/crops for the same GMO gene (e.g. CP4 EPSPS) having different levels of GMO protein. Specifically, the CP4 EPSPS (GMO protein) content was evaluated through ELISA by testing several "100%" GMO Certified Reference Materials (CRM). Importantly, a single species % GMO standard cannot accurately be used in complex matrices like foods and supplements that potentially have several GMO transformation events from different species. Thus, purified GMO protein is a universal standard for all events containing this protein and the results are reported quantitatively as w/w (ng/g).

Example 6

Comparative Example Involving Food Processing

GMO testing of dietary supplement and food matrices are complex, thus it is useful to test for both genes and proteins in case sample processing makes detection of one unreliable. A GMO cookie was prepared using the ingredients listed in Table 4. The cookie was baked at 375° C. for 20 minutes. A comparison of GMO protein and GMO gene expression between the uncooked and cooked cookie. GMO proteins were not consistently detected in the cooked cookie product because the cooking process denatured the protein of interest to a form that was unrecognizable by the capture antibody in the ELISA assay. However, the common GMO gene elements were detected (positive) in the cooked and uncooked cookie showing that both products contained GMO (see Table 5).

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

Thermal Cycler Conditions
Lid: 105° C.; Volume: 40 µl

| Steps | Temperature | Time | Ramp Rate | Cycles |
|---|---|---|---|---|
| 1 | 95° C. | 10 min | 2° C./sec | 1 |
| 2 | 94° C. | 30 sec | 2° C./sec | 1 |
| 3 | 58° C. | 1 min | 2° C./sec | 1 |
| 4 | Repeat Step 2 and 3, 39 times for a total of 40 cycles | | | 39 |
| 5 | 98° C. | 10 min | 2° C./sec | 1 |
| 6 | 8° C. | ∞ | 1° C./sec | ∞ |

TABLE 2

Dietary supplement samples tested for GMO genes (P35S, TNOS, P34S) by RT-qPCR and ddPCR.

| Sample # | RT-qPCR | | | ddPCR | | |
|---|---|---|---|---|---|---|
| | P35S | TNOS | P34S | P35S | TNOS | P34S |
| 1 | negative | positive, Cq 38/— | negative | negative | negative | negative |
| 2 | positive, Cq 41/43 | negative | negative | negative | negative | negative |
| 3 | positive, Cq 37/38 | negative | positive, Cq 36/38 | negative | negative | negative |
| 4 | negative | negative | positive, Cq 37/— | negative | negative | negative |
| 5 | positive, Cq 38/— | negative | negative | negative | negative | negative |
| 6 | negative | negative | positive, Cq 40/— | negative | negative | negative |
| 7 | positive, Cq 37/37 | positive, Cq 39/39 | negative | negative | negative | negative |

TABLE 3

CP4 EPSPS (GMO Protein) ELISA results from testing several '100%' GMO Certified Reference Materials (CRM).

| Sample # | Type of GMO Crop | % of GMO Material containing CP4 EPSPS* |
|---|---|---|
| 1 | Soybean, variety 1 | 304 |
| 2 | Soybean, variety 2 | 1.2 |
| 3 | Corn, variety 1 | 14.12 |
| 4 | Corn, variety 2 | 13.02 |
| 5 | Canola, variety 1 | 140 |
| 6 | Canola, variety 2 | 104 |

TABLE 4

The composition of the in-house GMO cookie.

| Ingredient | % Composition |
|---|---|
| GMO soybeans, variety 1 | 3 |
| GMO soybeans, variety 2 | 1 |
| GMO corn, variety 1 | 1.5 |
| GMO corn, variety 2 | 2 |
| Organic Soybeans | 19.03 |

TABLE 4-continued

The composition of the in-house GMO cookie.

| Ingredient | % Composition |
|---|---|
| Organic Corn | 19.61 |
| Organic Flour | 53.86 |
| | 100% |

TABLE 5

Cooked and Uncooked GMO Cookie Product Result Comparison.

| Transgenic marker | Cooked Cookie Finished Product | Uncooked Cookie Finished Product | % Recovery of Analyte in Finished Product |
|---|---|---|---|
| Cry1Ab protein (ng/g) | <LOQ | <LOQ | NA |
| Cry2Ab protein (ng/g) | <LOQ | 407.15 | 0 |
| Cry34Ab1 protein (ng/g) | 6.15 | 195.76 | 3 |
| Cry1Ac protein (ng/g) | <LOQ | 440.85 | 0 |
| Cry3Bb protein (ng/g) | <LOQ | 884.4 | 0 |
| Cry1F protein (ng/g) | <LOQ | 37.8 | 0 |
| VIP3a protein (ng/g) | <LOQ | <LOQ | NA |
| NPTII protein (ng/g) | <LOQ | <LOQ | NA |
| PMI protein (ng/g) | <LOQ | 124.69 | 0 |
| CP4 EPSPS protein (ng/g) | <LOQ | 383.59 | 0 |
| PAT protein (ng/g) | <LOQ | <LOQ | NA |
| P35S Promoter/CaMV DNA element | positive | positive | NA |
| NOS Terminator/A. tumefaciens DNA element | positive | positive | NA |
| P34S Promoter/FMV DNA element | positive | positive | NA |

NA: not applicable;
LOQ: limit of quantification

TABLE 6

Interpretation of Cumulative GMO Protein and DNA Results

| Protein | GMO Protein | DNA | GMO DNA | Interpretation |
|---|---|---|---|---|
| + | − | + | − | No GMO protein or GMO DNA elements present |
| − | + | − | − | No GMO protein or GMO DNA elements present (protein is false positive) |
| − | − | − | − | No protein or DNA to test |
| + | + | + | − | GMO protein but no GMO DNA present |
| + | + | + | + | GMO protein and DNA elements present |
| + | + | − | + | GMO proteins present but no plant GMO DNA elements |
| − | − | + | + | GMO gene elements present, but not GMO protein |
| + | − | + | + | GMO gene elements present, but not GMO protein |

FULL CITATION FOR DOCUMENTS REFERRED TO IN THE APPLICATION

1. Sticklent M. Plant genetic engineering to improve biomass characteristics for biofuels. *Curr. Opin. Biotechnol.* 2005. 17:315-319.
2. Conrad U. Polymers from plants to develop biodegradable plastics. *Trends. Plant. Sci.* 2005. 10:511-512.
3. Ma J. K. C., Drake P. M. W., Christou P. The production of recombinant pharmaceutical proteins in plant. *Nature.* 2003. 4:794-805.

4. Key S., Ma J. K. C., Drake P. M. W. Genetically modified plants and human health. *J. R. Soc. Med.* 2008. 101:290-298.

The invention claimed is:

1. A method for testing a sample for the presence of Genetically Modified Organism (GMO) material comprising:
   (i) homogenizing the sample by one of:
      (a) if the sample is a solid, grinding the solid to a powder,
      (b) if the sample is a semi-solid, freezing the sample and grinding frozen sample to a powder, and
      (c) if the sample is a liquid, agitating the sample if necessary for homogenization;
   (ii) extracting DNA from a portion of the sample obtained in (i);
   (iii) extracting protein from a portion of the sample obtained in (i);
   (iv) confirming a presence of DNA in the extract obtained in (ii) and if DNA is present, performing a PCR amplification on the extract to detect the presence of GMO gene elements in the extract, wherein the GMO gene elements comprise P35S promoter from cauliflower mosaic virus (CaMV), NOS terminator from *A. tumefaciens* and P34S promoter from figwort mosaic virus (FMV); and
   (v) confirming a presence of protein in the extract obtained in (iii) and if protein is present, performing an immunoassay on the extract to detect the presence of GMO proteins in the extract, wherein the GMO proteins comprise Cry1Ab, Cry2Ab, Cry34Ab1, Cry1Ac, Cry3Bb, Cry1F, VIP3a, NPTII, PMI, CP4 EPSPS and PAT,
   wherein the immunoassay comprises detecting a plurality of protein standards to obtain a standard curve and the method quantifies an amount of the GMO proteins as a weight of GMO protein per weight of the sample (w/w) using the standard curve.

2. The method of claim 1, wherein the plurality of protein standards comprises a dilution series of three or more dilutions for each GMO protein.

3. The method of claim 1, wherein the protein standards and the presence the GMO proteins in the sample are detected concurrently.

4. The method of claim 1, wherein the immunoassay is an Enzyme-Linked Immunosorbent Assay (ELISA).

5. The method of claim 4, wherein the ELISA comprises separate incubations with a capture antibody and a detection antibody.

6. The method of claim 1, wherein the immunoassay has a detection limit of at least 4 parts per billion (ppb) for one or more of the GMO proteins.

7. The method of claim 1, wherein the immunoassay has a detection limit of at least at least 10 ppb for one or more of the GMO proteins.

8. The method of claim 1, further comprising detecting a level of total protein in the sample.

9. The method of claim 8, wherein detecting the level of total protein in the sample comprises a Bradford assay and/or SDS-PAGE.

10. The method of claim 1, wherein if valid results are not obtained in the PCR amplification of step (iv) the method comprises:
    adjusting the extraction of DNA from the sample in step (ii) or adjusting the PCR amplification of step (iv); and
    retesting the sample for the presence of the GMO gene elements,
    wherein the adjusting the extraction of DNA from the sample comprises extracting DNA from >100 mg of the sample, eluting DNA in a smaller volume of water to provide a more concentrated sample, and/or performing a second DNA elution.

11. The method of claim 10, wherein if valid results are not obtained in the immunoassay of steps (v):
    adjusting the extraction of protein from the sample in step (iii) or adjusting the immunoassay of step (v); and
    retesting the sample for the presence or absence of the GMO proteins,
    wherein the adjusting the immunoassay assay comprises adjusting the pH to an optimal range and/or removing heavy metals, optionally using dialysis.

12. The method of claim 1, wherein the plurality of protein standards comprises a dilution series of five or more dilutions for each GMO protein.

13. The method of 1, wherein the plurality of protein standards and the presence of the GMO proteins in the sample are detected on the same plate.

14. The method of claim 1, wherein, when the sample is a raw material the GMO gene elements are detected using RT-PCR and when the sample is a baked good or a processed food, the GMO gene elements are detected using ddPCR.

15. The method of claim 1, further comprising generating a summary indicative of the presence GMO material in the sample based on results from steps (iv) and (v).

16. The method of claim 1, wherein the sample is a food product or an ingredient in the food product and the method further comprises labelling the food product based on results from steps (iv) and (v).

17. The method of claim 16, wherein if the method does not detect GMO material the food product the product is labeled as GMO-free.

18. The method of claim 1, further comprising treating the sample to remove PCR inhibitors prior to (iv).

* * * * *

UNITED STATES PATENT AND TRADEMARK OFFICE
CERTIFICATE OF CORRECTION

| | |
|---|---|
| PATENT NO. | : 11,060,126 B2 |
| APPLICATION NO. | : 15/998965 |
| DATED | : July 13, 2021 |
| INVENTOR(S) | : Olga Akimova et al. |

It is certified that error appears in the above-identified patent and that said Letters Patent is hereby corrected as shown below:

In the Claims

1. Column 18, Line 2, "a detection limit of at least at least 10 ppb", should read -- "a detection limit of at least 10 ppb" --

2. Column 18, Line 33, "The method of 1, wherein", should read -- "The method of claim 1" --.

3. Column 18, Line 48, "not detect GMO material the food product the product is", should read -- "not detect GMO material the food product is" --

Signed and Sealed this
Fourth Day of April, 2023

Katherine Kelly Vidal
*Director of the United States Patent and Trademark Office*